US011666872B2

(12) United States Patent
Suchocki et al.

(10) Patent No.: US 11,666,872 B2
(45) Date of Patent: *Jun. 6, 2023

(54) CONTAINERS FOR AGITATION OF LIQUID SAMPLES AND METHODS OF USE THEREOF

(71) Applicant: T2 Biosystems, Inc., Lexington, MA (US)

(72) Inventors: Adam Suchocki, Lexington, MA (US); Mark John Audeh, Brighton, MA (US); Matthew Blanco, Brookline, MA (US); James Franklin Chepin, San Diego, CA (US); Vasiliki Demas, Arlington, MA (US); Marilyn Lee Fritzemeier, Lexington, MA (US); Thomas Jay Lowery, Jr., Belmont, MA (US); Michael Min, Boston, MA (US); Lori Anne Neely, Reading, MA (US); Charles William Rittershaus, Malden, MA (US); Hwa-Tang Wang, Lexington, MA (US); Parris Wellman, Reading, MA (US)

(73) Assignee: T2 Biosystems, Inc., Lexington, MA (US)

( * ) Notice: Subject to any disclaimer, the term of this patent is extended or adjusted under 35 U.S.C. 154(b) by 379 days.

This patent is subject to a terminal disclaimer.

(21) Appl. No.: 16/659,215

(22) Filed: Oct. 21, 2019

(65) Prior Publication Data

US 2020/0261873 A1    Aug. 20, 2020

Related U.S. Application Data

(60) Continuation of application No. 15/453,356, filed on Mar. 8, 2017, now Pat. No. 10,486,118, which is a (Continued)

(51) Int. Cl.
*C12N 1/06* (2006.01)
*B01F 29/30* (2022.01)
(Continued)

(52) U.S. Cl.
CPC ............ *B01F 29/30* (2022.01); *B01F 33/251* (2022.01); *B01F 35/53* (2022.01);
(Continued)

(58) Field of Classification Search
CPC ............................... C12M 47/06; C12N 1/066
(Continued)

(56) References Cited

U.S. PATENT DOCUMENTS 2,794,627 A    6/1957 Rodwick
4,295,613 A    10/1981 Moore et al.
(Continued)

FOREIGN PATENT DOCUMENTS

EP           0224650 A2    6/1987
WO    WO-2011/034621 A2    3/2011
WO    WO-2012/054639 A2    4/2012

OTHER PUBLICATIONS

Extended European Search Report for European Application No. 13751876.7, dated Oct. 28, 2015 (8 pages).
(Continued)

*Primary Examiner* — David L Sorkin
(74) *Attorney, Agent, or Firm* — Clark & Elbing LLP

(57) ABSTRACT

The present invention relates to containers for holding liquid samples. The containers may be useful for mixing a liquid sample or lysing cells in a liquid sample. The invention also relates to methods of using the containers of the invention.

18 Claims, 16 Drawing Sheets

Related U.S. Application Data division of application No. 13/650,734, filed on Oct. 12, 2012, now Pat. No. 9,707,528.

(60) Provisional application No. 61/601,842, filed on Feb. 22, 2012.

(51) Int. Cl.

| | |
|---|---|
| *G01N 27/74* | (2006.01) |
| *G01N 33/49* | (2006.01) |
| *C12M 1/00* | (2006.01) |
| *B65D 1/46* | (2006.01) |
| *C12Q 1/6816* | (2018.01) |
| *C12Q 1/686* | (2018.01) |
| *B01F 33/25* | (2022.01) |
| *B01F 35/53* | (2022.01) |

(52) U.S. Cl.
CPC ............ *B01F 35/5312* (2022.01); *B65D 1/46* (2013.01); *C12M 47/06* (2013.01); *C12N 1/066* (2013.01); *C12Q 1/686* (2013.01); *C12Q 1/6816* (2013.01); *G01N 27/745* (2013.01); *G01N 33/492* (2013.01); *B01F 2215/0431* (2013.01); *B65D 2221/00* (2013.01)

(58) Field of Classification Search
USPC .............................................. 241/2
See application file for complete search history.

(56) References Cited

U.S. PATENT DOCUMENTS

| | | | |
|---|---|---|---|
| 4,690,153 | A | 9/1987 | Losada et al. |
| 5,374,522 | A | 12/1994 | Murphy et al. |
| 5,422,273 | A | 6/1995 | Garrison et al. |
| 7,377,027 | B2 | 5/2008 | Mayer |
| D696,398 | S | 12/2013 | Blanco et al. |
| 9,707,528 | B2 * | 7/2017 | Suchocki ................ B65D 1/46 |
| 2010/0291536 | A1 | 11/2010 | Viljoen et al. |
| 2011/0107855 | A1 | 5/2011 | Motadel |
| 2012/0196313 | A1 | 8/2012 | Williams et al. |

OTHER PUBLICATIONS

International Search Report and Written Opinion for International Patent Application No. PCT/US13/27068, dated Apr. 23, 2013 (13 pages).

Verollet, "A major step towards efficient sample preparation with bead-beating," Biotechniques. 44(6):832-3 (2008).

* cited by examiner

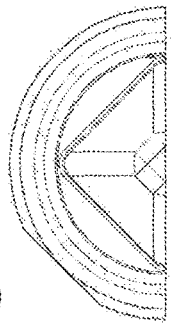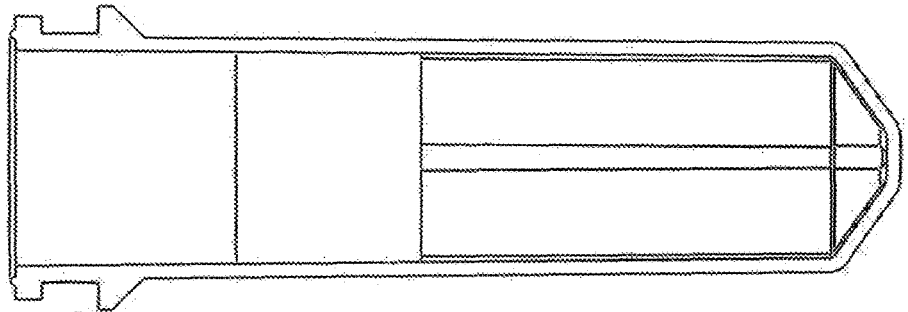
Fig. 8A  Fig. 8B
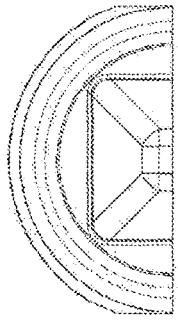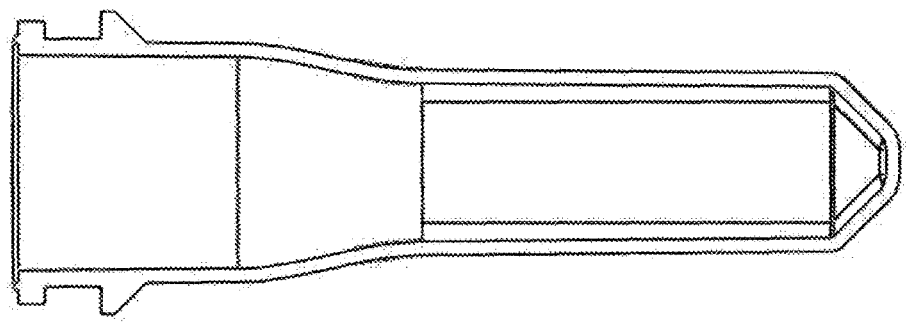
Fig. 8C  Fig. 8D

CONTAINERS FOR AGITATION OF LIQUID SAMPLES AND METHODS OF USE THEREOF

CROSS-REFERENCE TO RELATED APPLICATIONS

This application claims the benefit of the filing date of U.S. Provisional Application No. 61/601,842, filed Feb. 22, 2012, herein incorporated by reference in its entirety.

BACKGROUND OF THE INVENTION

Standard biochemical and molecular biological assays often require that a liquid sample is mixed and/or that its cellular contents are lysed at one or more steps in the assay. Previously, in order to mix a liquid sample, the sample is placed in a container, which is then positioned on an agitation device. The agitation device shakes the container, thereby mixing the liquid contents of the container. Lysing of cells in a liquid sample may involve the addition of micron-sized, rigid particles to the sample prior to the mixing step. In this agitation process, known as bead beating, the rigid particles disrupt the cell wall with productive collisions, thereby lysing the cells.

Conventionally, a sample container has a circular interior chamber with a smooth surface. Although ideal for some uses, the smooth surface may hinder efficient mixing or lysing. For example, rather than making numerous productive collisions with the cellular components of the liquid sample, the rigid particles used in bead beating may primarily travel in a circle in the interior diameter of the container, generating few productive collisions. Therefore, there is an unmet need in the field to develop methods for increasing the efficiency with which a liquid sample can be mixed and/or its cellular components can be lysed.

SUMMARY OF THE INVENTION

The present invention relates to containers for mixing and cell lysis operations in a laboratory environment. In one aspect, the invention features a container (e.g., a tube) including an interior chamber with a central axis, a top including an opening, and a substantially circular cross section, wherein the surface of the interior chamber includes one or more substantially linear protrusions substantially parallel to the central axis.

In another aspect, the invention features a container (e.g., a tube) including an interior chamber with a central axis, a top including an opening, and a substantially polygonal cross section having a radius, wherein the radius is the distance from the central axis to a corner point. In some embodiments of the second aspect, the surface of the interior chamber includes one or more substantially linear protrusions substantially parallel to the central axis. In other embodiments, the substantially polygonal cross section is substantially triangular, quadrilateral, pentagonal, hexagonal, heptagonal, octagonal, nonagonal, decagonal, or dodecagonal.

The above-containers can have, e.g., a volume less than 5 mL (e.g., 4, 3, 2, 1.5, 1, 0.5 mL, or less). In certain embodiments, the container can have a volume of 2.8 mL.

The above-containers can have one or more protrusions with a length parallel to the central axis, a depth substantially parallel to the radius of the substantially circular or polygonal cross section, and a width substantially perpendicular to the radius. In one embodiment, the depth and/or width are constant or vary along the length of the substantially linear protrusion. In another embodiment, the depth and/or width increases from top to bottom of the substantially linear protrusion. In some embodiments, the depth is greater than 10% of the radius (e.g., 11%, 12%, 13%, 14%, 15%, 16%, 17%, 18%, 19%, 20%, 30%, 40%, 50%, or 60% of the radius) at some point along the length of the substantially linear protrusion. In some embodiments, the depth is greater than 20% of the radius (e.g., 21%, 22%, 23%, 24%, 25%, 26%, 27%, 28%, 29%, 30%, 40%, 50%, 60%, or 70% of the radius) at some point along the length of the substantially linear protrusion. In some embodiments, the depth is greater than 30% of the radius (e.g., 31%, 32%, 33%, 34%, 35%, 36%, 37%, 38%, 39%, 40%, 50%, 60%, 70%, or 80% of the radius) at some point along the length of the substantially linear protrusion. In other embodiments, the depths of the top and bottom of the substantially linear protrusion are at least between 0.3 to 0.5 millimeters (mm) (e.g., at least between 0.3 to 0.35 mm, at least between 0.35 to 0.4 mm, at least between 0.4 to 0.45 mm, or at least between 0.45 to 0.5 mm) and 0.75 to 1 mm (e.g., at least between 0.75 to 0.8 mm, at least between 0.8 to 0.85 mm, at least between 0.85 to 0.9 mm, at least between 0.9 to 0.95 mm, or at least between 0.95 to 1 mm), respectively. In other embodiments, the depths of the top and bottom of the substantially linear protrusion are at least between 0.75 to 1.25 mm (e.g., at least between 0.75 to 0.9 mm, at least between 0.9 to 1 mm, at least between 1 to 1.1 mm, or at least between 1.1 to 1.25 mm) and 1.75 to 2.25 mm (e.g., at least between 1.75 to 1.9 mm, at least between 1.9 to 2 mm, at least between 2 to 2.1 mm, or at least between 2.1 to 2.25 mm), respectively.

The foregoing containers of the invention may have protrusions with a distal length and a proximal length relative to the central axis, wherein the distal and proximal lengths are each between 40-95% of the height of the container (e.g., 40-50%, 50-60%, 60-70%, 70-80%, 80-90%, or 90-95% the height of the container). In certain embodiments, the proximal length may be equal to or greater than the distal length. In another embodiment, the one or more substantially linear protrusions are substantially trapezoidal. For example, the distal and proximal lengths are each at least around 15 mm. In other embodiments, the distal and proximal lengths are each at least around 30 mm.

Any of the foregoing containers may have protrusions with a width greater than 5% of the radius (e.g., 6%, 7%, 8%, 9%, 10%, or 25% of the radius) at some point along the length of the substantially linear protrusion. In some embodiments, the width is greater than 10% of the radius (e.g., 11%, 12%, 13%, 14%, 15%, or 30% of the radius) at some point along the length of the substantially linear protrusion. In some embodiments, the width is greater than 15% of the radius (e.g., 16%, 17%, 18%, 19%, 20%, or 35% of the radius) at some point along the length of the substantially linear protrusion. In other embodiments, the width is at least between 0.025 to 0.175 mm (e.g., at least between 0.025 to 0.075 mm, at least between 0.075 to 0.1 mm, at least between 0.1 to 0.15 mm, or at least between 0.15 to 0.175 mm) at some point along the length of the substantially linear protrusion. In other embodiments, the width is at least between 0.175 to 0.375 mm (e.g., at least between 0.175 to 0.225 mm, at least between 0.225 to 0.275 mm, at least between 0.275 to 0.325 mm, or at least between 0.325 to 0.375 mm) at some point along the length of the substantially linear protrusion. In other embodiments, the width is at least between 0.5 to 0.7 mm (e.g., at least between 0.5 to 0.55 mm, at least between 0.55 to 0.6 mm, at least between 0.6 to 0.65 mm, or at least between 0.65 to 0.7 mm) at some point along the length of the substantially linear protrusion.

In some embodiments, the foregoing containers may have protrusions that are angled towards the bottom of the container and away from the radius of the substantially circular or polygonal cross section by between about 10° to 50°, for example, between about 10° to 25°, between about 25° to 35°, or between about 35° to 50°.

The compositions of the invention may have an interior chamber including 2 to 6 substantially linear protrusions (e.g., 2, 3, 4, 5, or 6 substantially linear protrusions). In some embodiments, the interior chamber includes 2 to 4 substantially linear protrusions. In certain embodiments, the substantially linear protrusions are evenly spaced within the interior chamber of the container.

The foregoing containers of the invention may further include a cover (e.g., a cap, lid, or top). In one embodiment, the cover includes a passage that extends from its exterior surface to its interior surface. In another embodiment, the passage includes three evenly spaced slits (e.g., a tri-slit) that converge at a central axis of the cover. In another embodiment, the exterior surface of the cover includes one or more protuberances (e.g., 2, 3, 4, 5, or 6 protuberances) between each of the three evenly spaced slits. In yet another embodiment, the interior surface includes a weighted ring that encircles the three evenly spaced slits. In some embodiments, the one or more protuberances of the exterior surface and the weighted ring of the interior surface promote closure of the passage (e.g., closure upon breaching of the passage by, e.g., a pipette tip or a needle). In other embodiments, the interior chamber of the container can be accessed through the passage. The covers of the invention can, e.g., prevent escape of liquid from the container during agitation.

Any of the foregoing containers can be constructed out of a non-polystyrene material (e.g., polycarbonate).

In another aspect, the invention features a method of mixing liquid in a container, the method including agitating the liquid in any of the foregoing containers with, e.g., an agitation device (e.g., a vortexer, e.g., a vortexer agitating in a pulsed motion, e.g. vortexer agitating in a modified circular manner (e.g. planetary orbital)), thereby mixing the liquid in the container.

In yet another aspect, the invention features a method of mixing liquid in a container, the method including (i) providing liquid in any of the foregoing containers of the invention, where the container comprises inert rigid particles (e.g., beads, shards, glass rods, and glass disks), and (ii) agitating the liquid in the container with, e.g., an agitation device (e.g., a vortexer, e.g., a vortexer agitating in a pulsed motion), thereby mixing the liquid in the container.

In another aspect, the invention features a method of lysing cells in a liquid sample, the method including providing liquid in a container of the first or second aspect of the invention, where the liquid includes rigid particles and cells (e.g., fungal or yeast cells), and agitating the liquid in the container with, e.g., an agitation device (e.g., a vortexer, e.g., a vortexer agitating in a pulsed motion, e.g. vortexer agitating in a modified circular manner (e.g., planetary orbital), wherein the agitation is of a sufficient force and duration to lyse the cells.

In yet another aspect, the invention features a method for detecting the presence of a target nucleic acid in a whole blood sample, the method including: (i) providing an extract produced by lysing the red blood cells in a whole blood sample from a subject (e.g., a human), centrifuging the sample to form a supernatant and a pellet, discarding some or all of the supernatant, and resuspending the pellet; (ii) lysing cells in the extract, the lysing including combining the extract with rigid particles to form a mixture in any of the foregoing containers of of the invention, and agitating the mixture with, e.g., an agitation device (e.g., a vortexer, e.g., a vortexer agitating in a pulsed motion) to form a lysate; (iii) providing the lysate of step (ii) in a detection tube and amplifying the nucleic acids therein to form an amplified lysate solution including from 40% (w/w) to 95% (w/w) the target nucleic acid (e.g., from 40% to 60%, 60% to 80%, 80% to 90%, or 90% to 95% (w/w) target nucleic acid) and from 5% (w/w) to 60% (w/w) nontarget nucleic acid (e.g., from 5% to 20%, 20% to 35%, 35% to 40%, or 40% to 60% (w/w) target nucleic acid); and, optionally, (iv) detecting the amplified target nucleic acid.

The invention also features a method of amplifying a target nucleic acid by (i) providing an extract produced by lysing the red blood cells in a whole blood sample from a subject (e.g., a human), centrifuging the sample to form a supernatant and a pellet, discarding some or all of the supernatant, and resuspending the pellet; (ii) lysing cells in the extract, the lysing including combining the extract with rigid particles to form a mixture in any of the foregoing containers of of the invention, and agitating the mixture with, e.g., an agitation device (e.g., a vortexer, e.g., a vortexer agitating in a pulsed motion) to form a lysate; (iii) providing the lysate of step (ii) in a detection tube and amplifying the nucleic acids therein to form an amplified lysate solution including from 40% (w/w) to 95% (w/w) the target nucleic acid (e.g., from 40% to 60%, 60% to 80%, 80% to 90%, or 90% to 95% (w/w) target nucleic acid) and from 5% (w/w) to 60% (w/w) nontarget nucleic acid (e.g., from 5% to 20%, 20% to 35%, 35% to 40%, or 40% to 60% (w/w) target nucleic acid). In a related aspect, the invention features a method of preparing an amplified lysate solution by the above-method.

The foregoing method can further comprise: (iv) following step (iii), providing from $1 \times 10^6$ to $1 \times 10^{13}$ magnetic particles per milliliter (e.g., from $1 \times 10^6$ to $1 \times 10^8$, $1 \times 10^7$ to $1 \times 10^8$, $1 \times 10^7$ to $1 \times 10^9$, $1 \times 10^8$ to $1 \times 10^{10}$, $1 \times 10^9$ to $1 \times 10^{11}$, or $1 \times 10^{10}$ to $1 \times 10^{13}$ magnetic particles per milliliter) of the amplified lysate solution, wherein the magnetic particles have a mean diameter of from 700 nm to 1200 nm (e.g., from 700 to 850, 800 to 950, 900 to 1050, or from 1000 to 1200 nm) and binding moieties on their surface, the binding moieties operative to alter aggregation of the magnetic particles in the presence of the target nucleic acid or a multivalent binding agent; (v) placing the detection tube in a device, the device including a support defining a well for holding the detection tube including the magnetic particles and the target nucleic acid, and having an RF coil disposed about the well, the RF coil configured to detect a signal produced by exposing the liquid sample to a bias magnetic field created using one or more magnets and an RF pulse sequence; (vi) exposing the sample to a bias magnetic field and an RF pulse sequence; (vii) following step (vi), measuring the signal from the detection tube; and (viii) on the basis of the result of step (vii), detecting the target nucleic acid, wherein step (vii) is, e.g., carried out without any prior purification of the amplified lysate solution.

In some embodiments of the methods of the invention which use rigid inert particles for mixing or lysing, the rigid particles (e.g., beads, shards, glass rods, and glass disks) have a diameter of between about 0.1 mm to 1 mm (e.g, between about 0.1 to 0.3 mm, between about 0.3 to 0.5 mm, between about 0.5 to 0.7 mm, between about 0.7 to 0.9 mm, or between about 0.9 to 1 mm). In other embodiments, the rigid particles have a diameter of about 0.8 mm.

In any of the methods of the invention, the agitation device is a vortexer. In another embodiment, the vortexer agitates in a linear, planetary, vertical orbit, or pulsed motion.

Definitions

The terms "aggregation," "agglomeration," and "clustering" are used interchangeably in the context of the magnetic particles described herein and mean the binding of two or more magnetic particles to one another, e.g., via a multivalent analyte, multimeric form of analyte, antibody, nucleic acid molecule, or other binding molecule or entity. In some instances, magnetic particle agglomeration is reversible.

By "container" is meant a rigid shaped article with a top, bottom, and sides, wherein the top optionally contains an opening for access to an interior that is able to contain liquid, gaseous, and/or solid samples. It is not limited to any particular shape, and may, for example, have a cross-section with a square, rectangular, triangular, circular, or oval shape. In some embodiments, the container may have an openable top surface, for example, a lid, cover, or cap.

The term "magnetic particle" refers to particles including materials of high positive magnetic susceptibility such as paramagnetic compounds, superparamagnetic compounds, and magnetite, gamma ferric oxide, or metallic iron.

By "pulse sequence" or "RF pulse sequence" is meant one or more radio frequency pulses to be applied to a sample and designed to measure, e.g., certain NMR relaxation rates, such as spin echo sequences. A pulse sequence may also include the acquisition of a signal following one or more pulses to minimize noise and improve accuracy in the resulting signal value.

As used herein, the term "signal" refers to an NMR relaxation rate, frequency shift, susceptibility measurement, diffusion measurement, or correlation measurements.

Other features and advantages of the invention will be apparent from the following Detailed Description, the drawings, and the claims.

BRIEF DESCRIPTION OF THE DRAWINGS

FIG. 8A is a cut-away top perspective view of one example of a container with a substantially square cross section according to the present invention.

FIG. 8B is a cut-away side perspective view of the container in FIG. 8A, rotated by 90° along a vertical axis.

FIG. 8C is a cut-away top perspective view of the container in FIG. 8A, rotated by 45° along a horizontal axis.

FIG. 8D is a cut-away side perspective view of the container in FIG. 8C, rotated by 90° along a vertical axis.

Figure 1A:
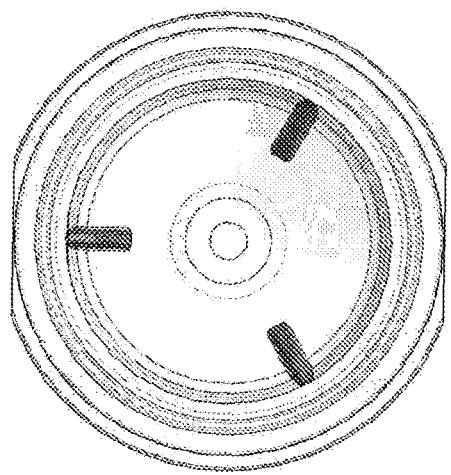
FIG. 1A is schematic top perspective view of one example of a container according to the present invention, showing the relative position of each substantially linear protrusion within the interior chamber of the container. The three linear protrusions are shaded gray for contrast. The container is depicted as semi-transparent.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

The present invention is based, at least in part, on containers for use in mixing or lysing cells in a liquid sample. A container may have an interior chamber with one or more (e.g., three, four, or five) substantially linear protrusions, which promote the mixing or lysing process. In some embodiments, rigid particles (e.g., beads) may be added to the liquid sample in the container (or be present in the container prior to the addition of a liquid) to additionally promote the mixing or lysing process. A container of the invention may also include a cover with a passage (e.g., a slit, e.g., a tri-slit) that can allow access to the interior chamber of the container while securely sealing the container top opening.

Containers for Mixing or Lysing

The interior chambers of the containers of the invention may have substantially circular cross sections with protrusions or substantially polygonal cross sections which optionally have protrusions. Both containers are particularly suited for efficiently mixing a liquid sample or lysing cells in a liquid sample.

Containers with Circular Cross Sections

A container of the present invention may include an interior chamber with a central axis, a top with an opening, and a substantially circular cross section, wherein the interior chamber includes one or more substantially linear protrusions (e.g., 2, 3, 4, 5, or 6 substantially linear protrusions) that are substantially parallel to the central axis. The container may be used to increase the efficiency of mixing a liquid sample or lysing cells in a liquid sample compared to a container without any linear protrusions. For example, the one or more substantially linear protrusions can promote the productive collisions of the rigid particles used in bead beating and prevent them from travelling in a circle during the agitation process, thereby increasing the efficiency of cell lysis.

Figure 6A:
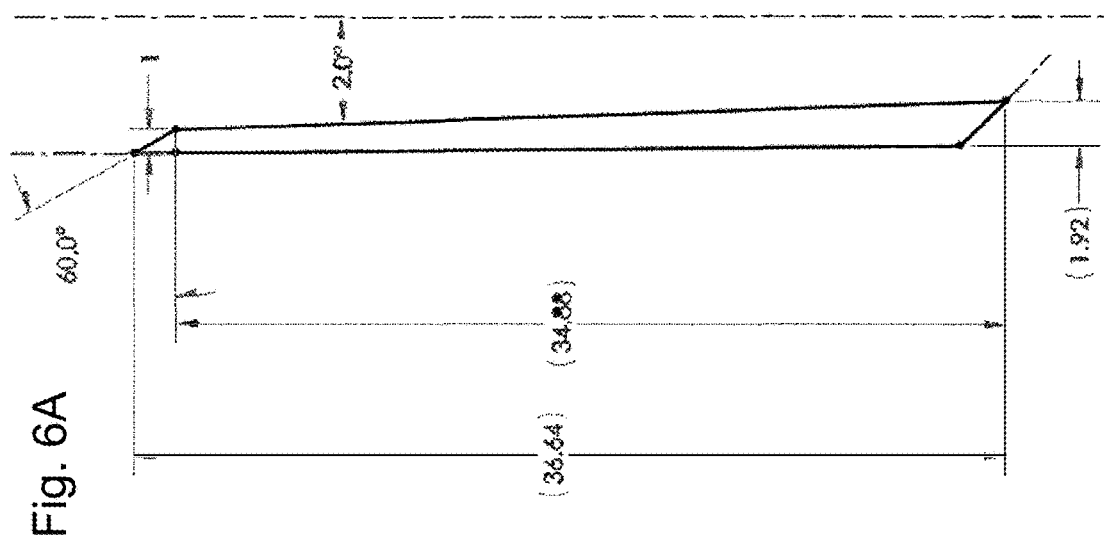
FIG. 6A is a drawing showing the relative length, depth, and tilt dimensions of one example of a substantially linear protrusion according to the present invention.
Figure 9D:
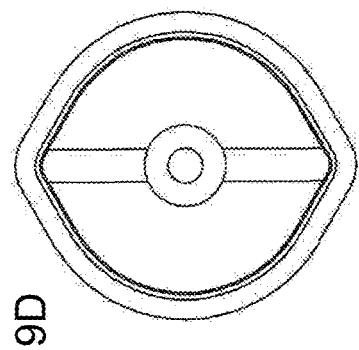
FIGS. 9C and 9D are schematic bottom perspective views of bottom-halves of containers with substantially circular cross sections having one or two indentations, respectively.
Figure 9C:
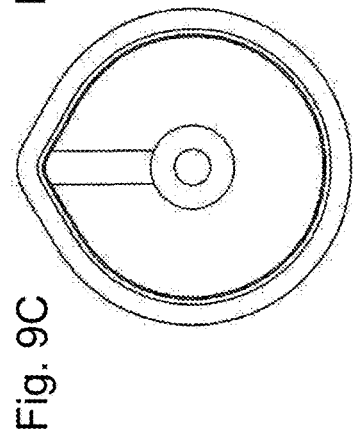
Figure 9A:
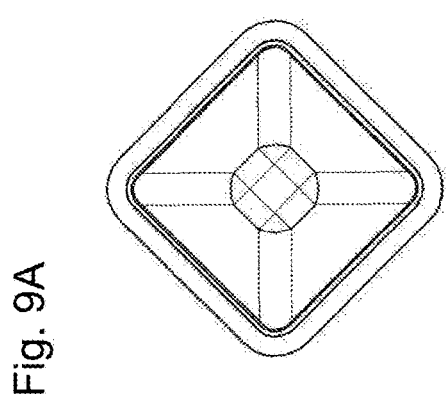
FIG. 9A is a schematic bottom perspective view of a bottom-half of a container with a substantially square cross section according to the present invention.
Figure 9G:
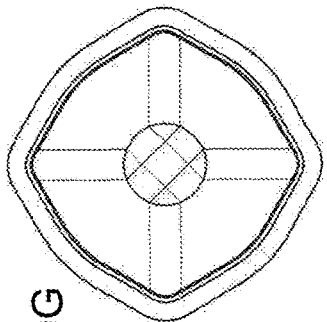
FIG. 9G is a schematic bottom perspective view of a bottom-half of a container with a substantially square cross section having curved sides.
Figure 9F:
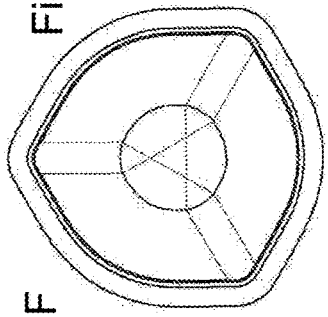
FIGS. 9E and 9F are schematic bottom perspective views of bottom-halves of containers with substantially triangular cross sections having straight or curved sides, respectively.
Figure 9E:
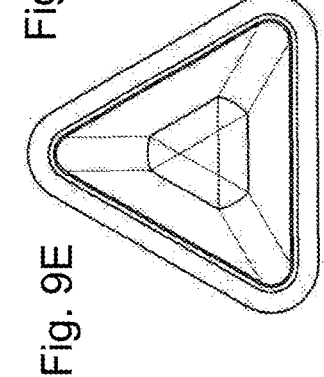
Figure 9J:
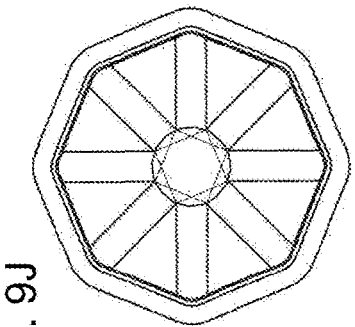
FIGS. 9H-9J are schematic bottom perspective views of bottom-halves of containers with substantially pentagonal, hexagonal, and octagonal sides.
Figure 9I:
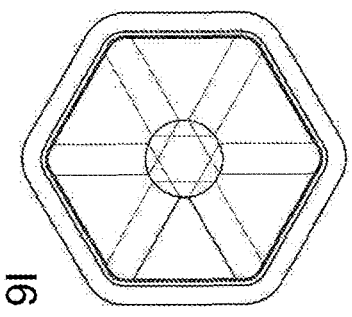
Figure 9H:
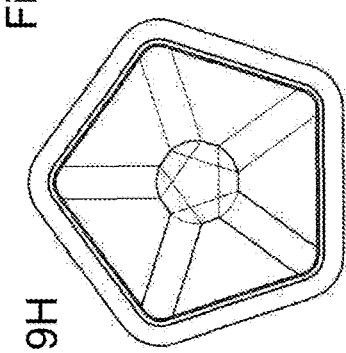
Figure 9B:
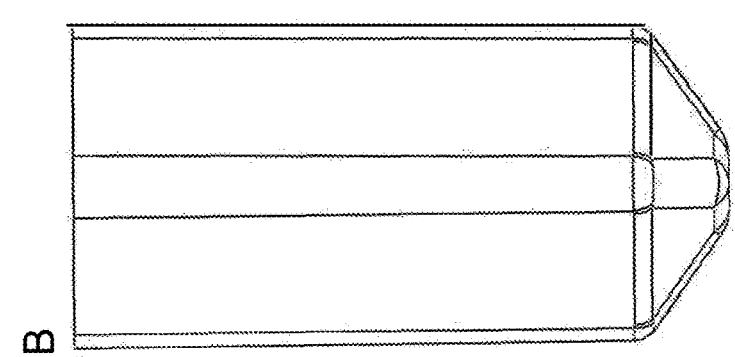
FIG. 9B is a schematic side perspective view of the bottom-half of a container in FIG. 9A, rotated by 90° along a vertical axis.

In some embodiments, the containers of the present invention with substantially circular cross sections have one or more substantially linear protrusions with a length parallel to the central axis, a depth substantially parallel to the radius of the substantially circular cross section, and a width substantially perpendicular to the radius. The depth and/or width may vary along the length of the linear protrusion. In some embodiments, the depth and/or width increases from top to bottom of the linear protrusion. The depth of the substantially linear protrusion may, for example, be greater than 10% of the radius (e.g., 11%, 12%, 13%, 14%, 15%, 16%, 17%, 18%, 19%, 20%, 30%, 40%, 50%, or 60% of the radius), greater than 20% of the radius (e.g., 21%, 22%, 23%, 24%, 25%, 26%, 27%, 28%, 29%, 30%, 40%, 50%, 60%, or 70% of the radius), or greater than 30% of the radius (e.g., 31%, 32%, 33%, 34%, 35%, 36%, 37%, 38%, 39%, 40%, 50%, 60%, 70%, or 80% of the radius) at some point along the length of the substantially linear protrusion. In other embodiments, the depths of the top and bottom of the substantially linear protrusions are at least between 0.3 to 0.5 millimeters (mm) (e.g., at least between 0.3 to 0.35 mm, at least between 0.35 to 0.4 mm, at least between 0.4 to 0.45 mm, or at least between 0.45 to 0.5 mm) and 0.75 to 1 mm (e.g., at least between 0.75 to 0.8 mm, at least between 0.8 to 0.85 mm, at least between 0.85 to 0.9 mm, at least between 0.9 to 0.95 mm, or at least between 0.95 to 1 mm), respectively; or at least between 0.75 to 1.25 mm (e.g., at least between 0.75 to 0.9 mm, at least between 0.9 to 1 mm, at least between 1 to 1.1 mm, or at least between 1.1 to 1.25 mm) and 1.75 to 2.25 mm (e.g., at least between 1.75 to 1.9 mm, at least between 1.9 to 2 mm, at least between 2 to 2.1 mm, or at least between 2.1 to 2.25 mm), respectively. Examples of containers of the invention with a circular cross section and three substantially linear protrusions, each with depth and width increasing from top to bottom of the protrusion, are depicted in detail in FIGS. 1A-5B. FIGS. 9C and 9D depict examples of containers of the invention with substantially circular cross sections. As depicted in FIG. 6A, a substantially linear protrusion may, for example, have a top and bottom depth of around 1 and 1.92 mm, respectively, which corresponds to around 18% and 35% of the radius of the container for a container with a radius of 5.5 mm.

The containers of the present invention with substantially circular cross sections may have one or more substantially linear protrusions which can vary in length. In some embodiments, the containers of the present invention with substantially circular cross sections have one or more substantially linear protrusions with a distal length and a proximal length relative to the central axis, wherein the distal and proximal lengths are each between 40-95% of the height of the container (e.g., 40-50%, 50-60%, 60-70%, 70-80%, 80-90%, or 90-95% the height of the container). In some embodiments, the proximal length may be greater than the distal length. The one or more substantially linear protrusions may thus be trapezoidal, whereby the edges that govern the depth of the protrusion are parallel, but the lengths are not. In some embodiments, the distal and proximal lengths are each at least 15 mm. In other embodiments, the distal and proximal lengths are each at least 30 mm. As depicted in FIGS. 1B, 3A, 3B, 5A, and 5B, the substantially linear protrusions may, for example, have lengths that span almost the entire height of the container, from near the top opening to close to the bottom of the container.

Figure 6B:
FIG. 6B is a drawing depicting width dimensions of one example of a substantially linear protrusion, viewed directly along the length of the protrusion.
Figure 7E:
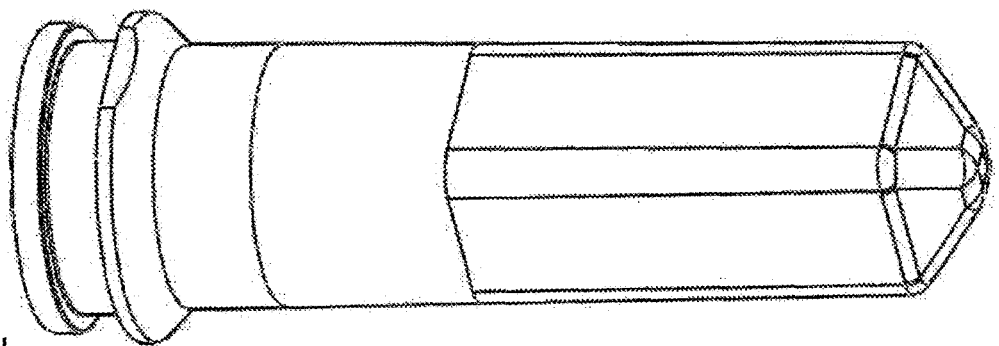
FIG. 7E is an angled schematic side perspective view of the container in FIG. 7A.
Figure 7D:
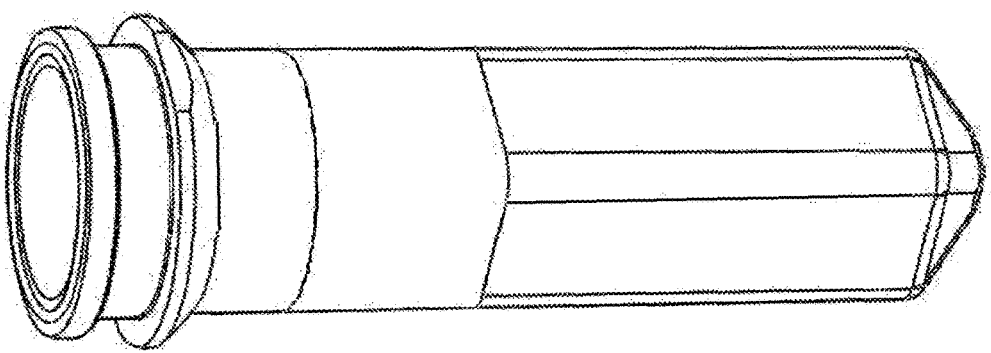
FIG. 7D is an angled schematic side perspective view of the container in FIG. 7A.
Figure 7A:
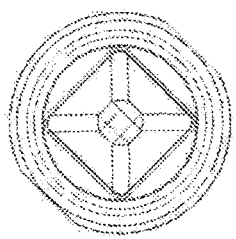
FIG. 7A is a schematic top perspective view of one example of a container with a substantially square cross section according to the present invention.
Figure 7B:
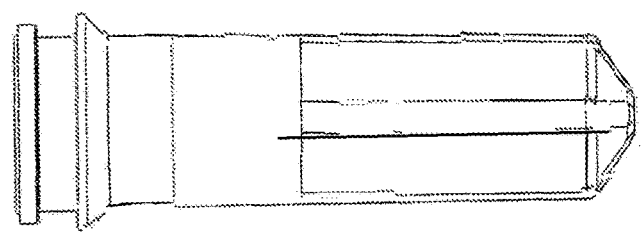
FIG. 7B is a schematic side perspective view of the container in FIG. 7A.
Figure 7C:
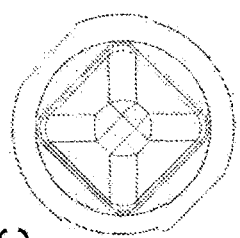
FIG. 7C is a schematic bottom perspective view of the container in FIG. 7A.

In some embodiments, the one or more substantially linear protrusions may have protrusions with a width greater than 5% of the radius (e.g., 6%, 7%, 8%, 9%, 10%, or 25% of the radius), greater than 10% of the radius (e.g., 11%, 12%, 13%, 14%, 15%, or 30% of the radius), or greater than 15% of the radius (e.g., 16%, 17%, 18%, 19%, 20%, or 35% of the radius) at some point along the length of the substantially linear protrusion. In other embodiments, the width is at least between 0.025 to 0.175 mm (e.g., at least between 0.025 to 0.075 mm, at least between 0.075 to 0.1 mm, at least between 0.1 to 0.15 mm, or at least between 0.15 to 0.175 mm), at least between 0.175 to 0.375 mm (e.g., at least between 0.175 to 0.225 mm, at least between 0.225 to 0.275 mm, at least between 0.275 to 0.325 mm, or at least between 0.325 to 0.375 mm), or at least between 0.5 to 0.7 mm (e.g., at least between 0.5 to 0.55 mm, at least between 0.55 to 0.6 mm, at least between 0.6 to 0.65 mm, or at least between 0.65 to 0.7 mm) at some point along the length of the substantially linear protrusion. As depicted in FIG. 6B, a substantially linear protrusion may, for example, have a width which increases along the length of the protrusion to a maximum width of 0.635 mm, or around 11.5% of the radius of the container for a container with a radius of 5.5 mm.

In some embodiments, e.g., as depicted in FIGS. 1B, 3A, 3B, 5A, and 5B, the substantially linear protrusions of the depicted containers are angled down towards the bottom of the container and away from the radius of the substantially circular cross section by between about 10° to 50° (e.g., between about 10° to 25°, between about 25° to 35°, or between about 35° to 50°). As depicted in FIG. 6A, a substantially linear protrusion may, for example, be angled downward by 30°, which is reflected in a 60° angle formed by the top depth and distal length of the linear protrusion rather than a 90° angle, in the case in which a protrusion is not angled.

Figure 1B:
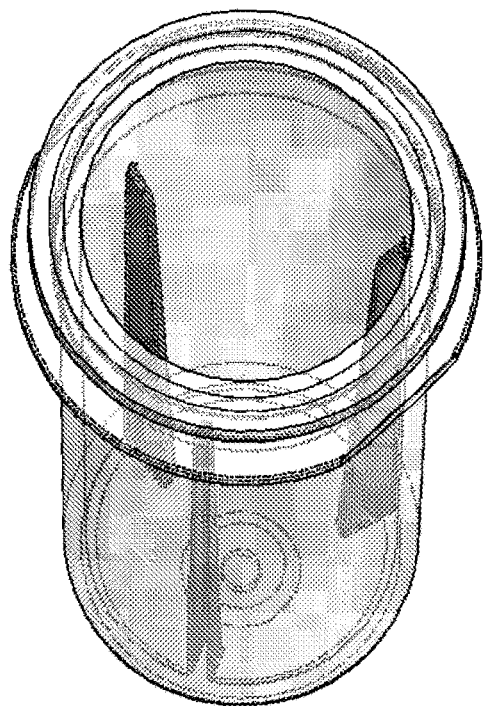
FIG. 1B is an angled schematic top perspective view of the container in FIG. 1A. The three linear protrusions are shaded gray for contrast. The container is depicted as semi-transparent.
Figure 2A:
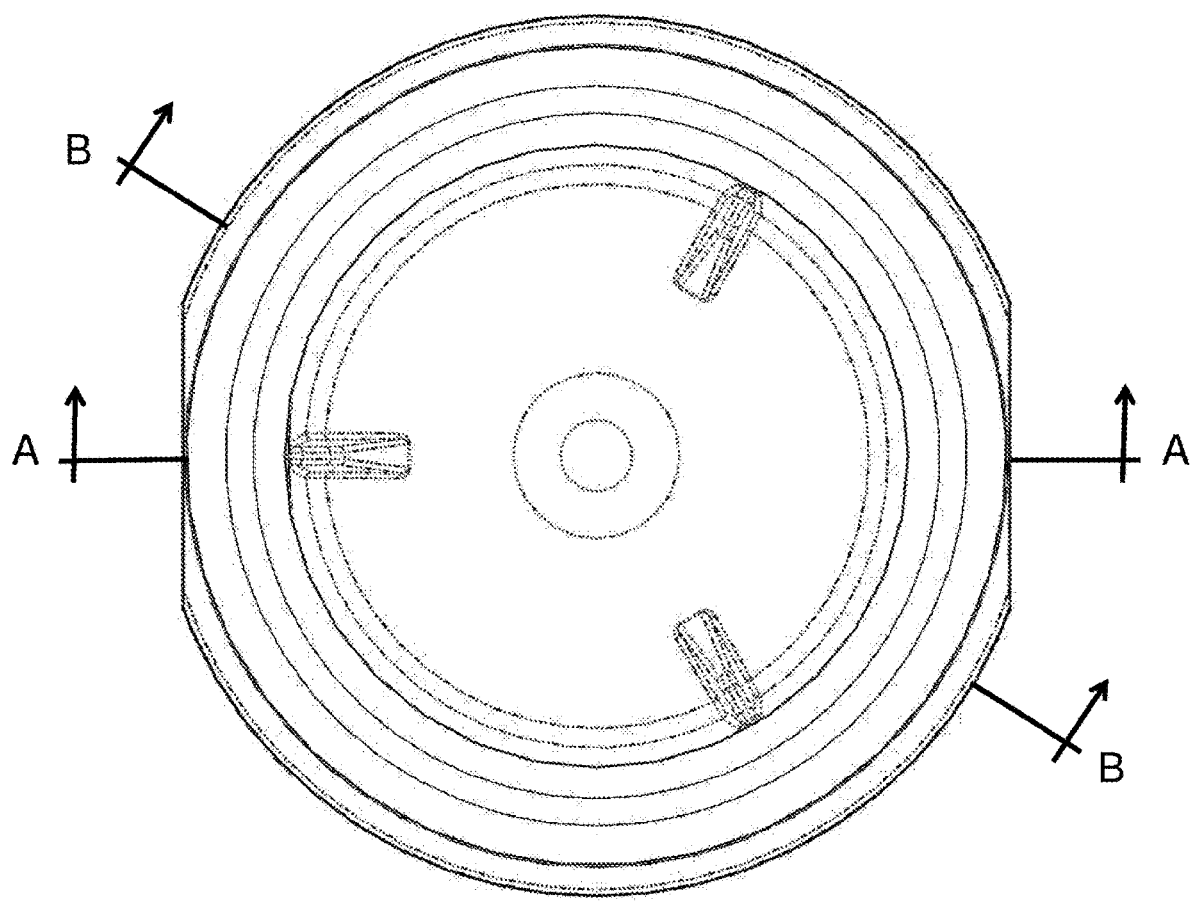
FIG. 2A is an enlarged schematic top perspective view of one example of a container according to the present invention, showing the relative position of each substantially linear protrusion within the interior chamber of the container.
Figure 2B:
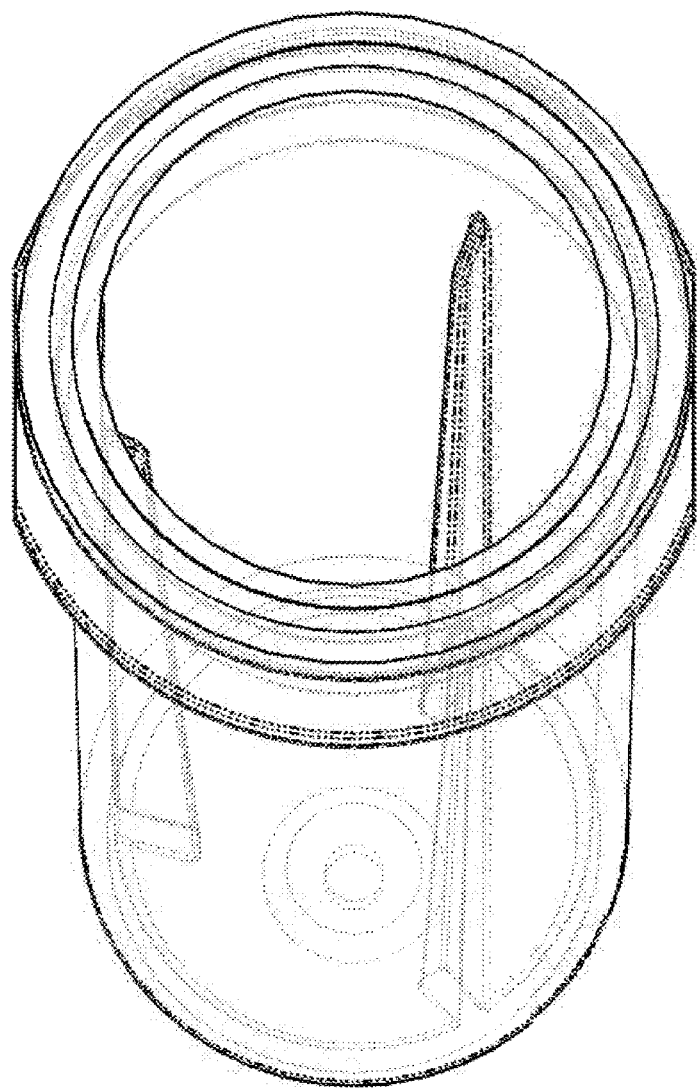
FIG. 2B is an enlarged angled schematic top perspective view of the container in FIG. 2A. The container is depicted as semi-transparent.
Figure 2C:
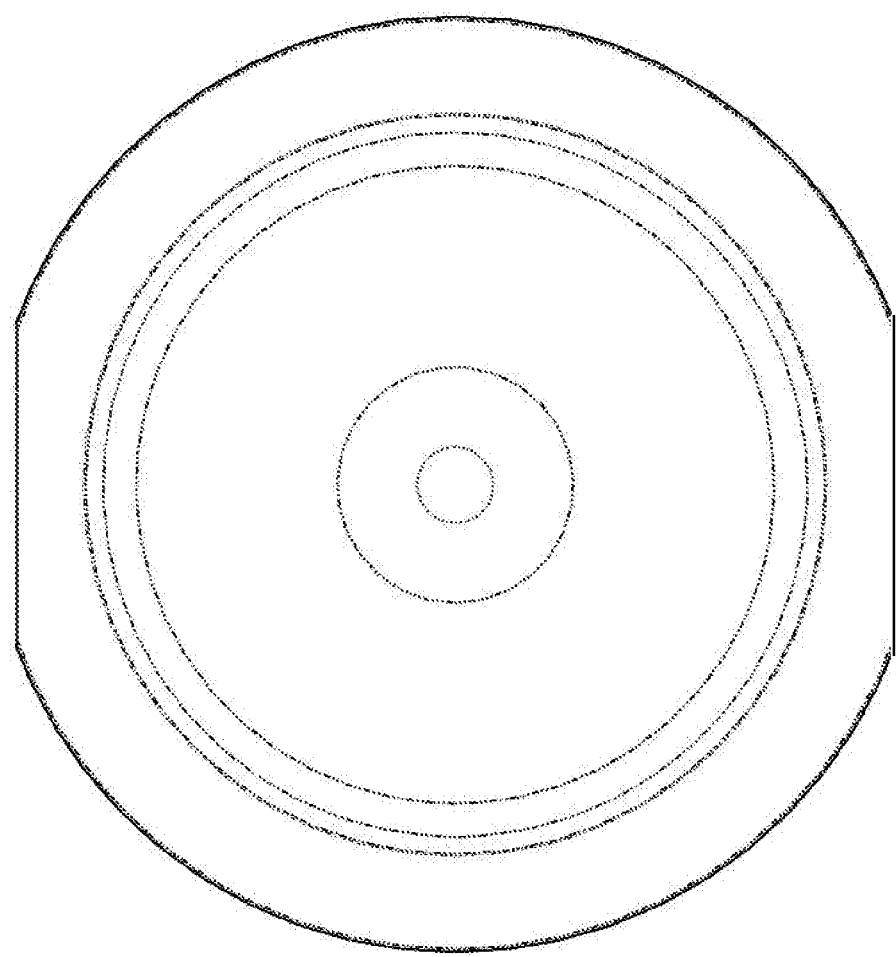
FIG. 2C is an enlarged schematic bottom perspective view of the container in FIG. 2A.
Figure 3A:
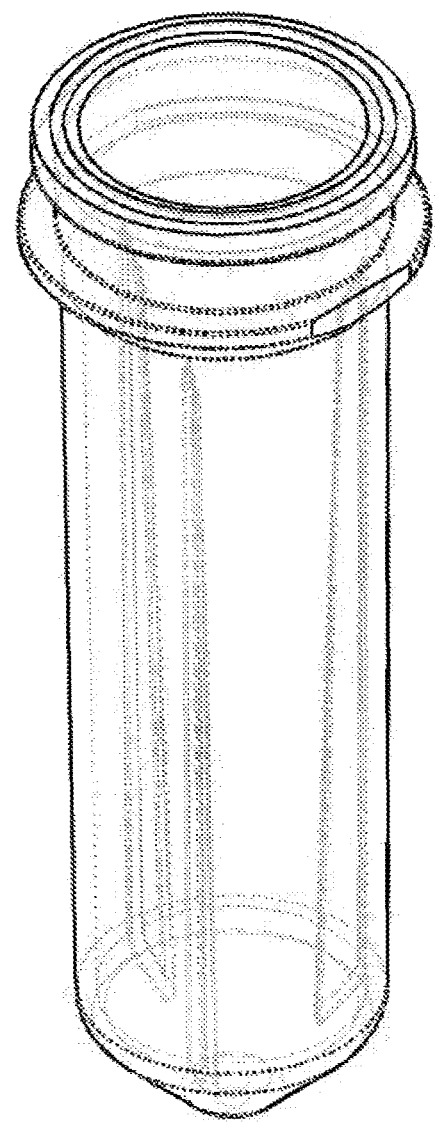
FIG. 3A is an angled schematic side perspective view of one example of a container according to the present invention. The container is depicted as semi-transparent.
Figure 3B:
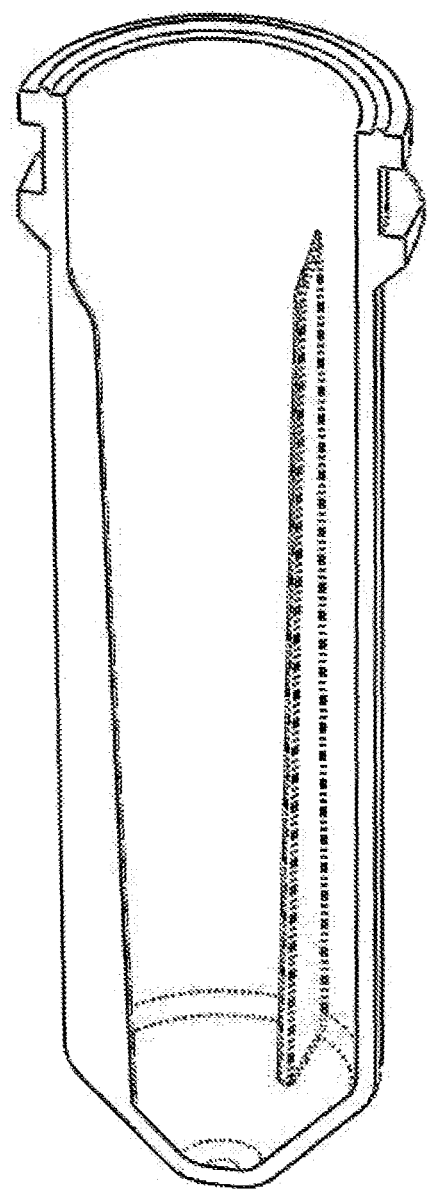
FIG. 3B is an angled cut-away side perspective view of the container in FIG. 3A.
Figure 4A:
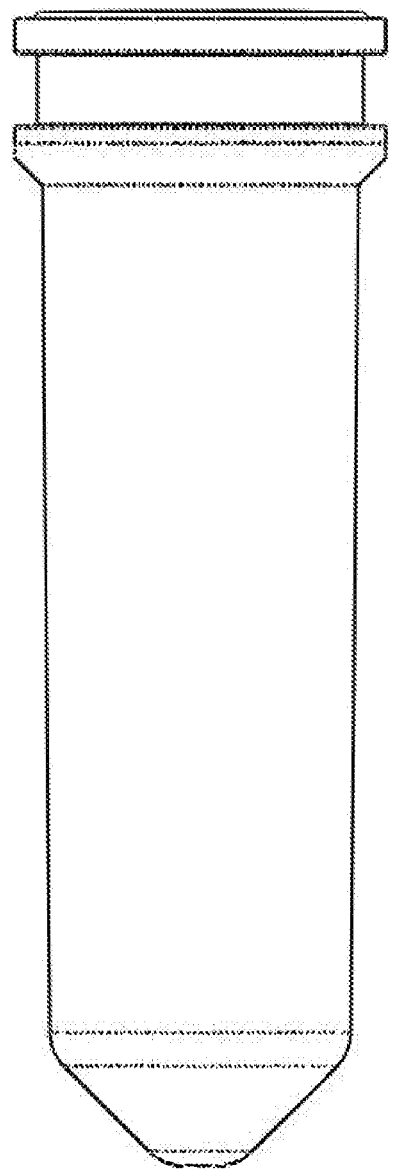
FIG. 4A is a schematic side perspective view of one example of a container according to the present invention. The container is not depicted as semi-transparent.
Figure 4B:
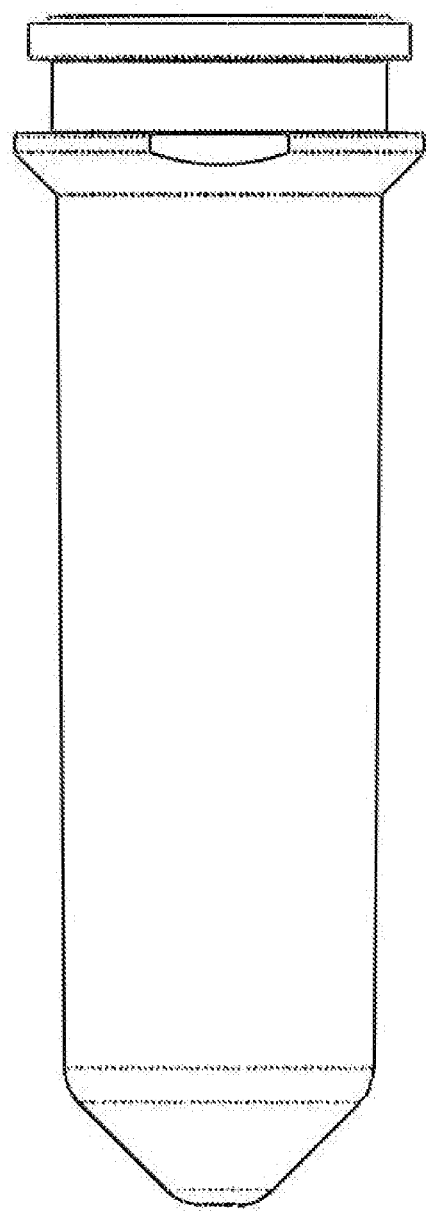
FIG. 4B is a schematic side perspective view of the container in FIG. 4A, rotated by 90° along a vertical axis.
Figure 5A:
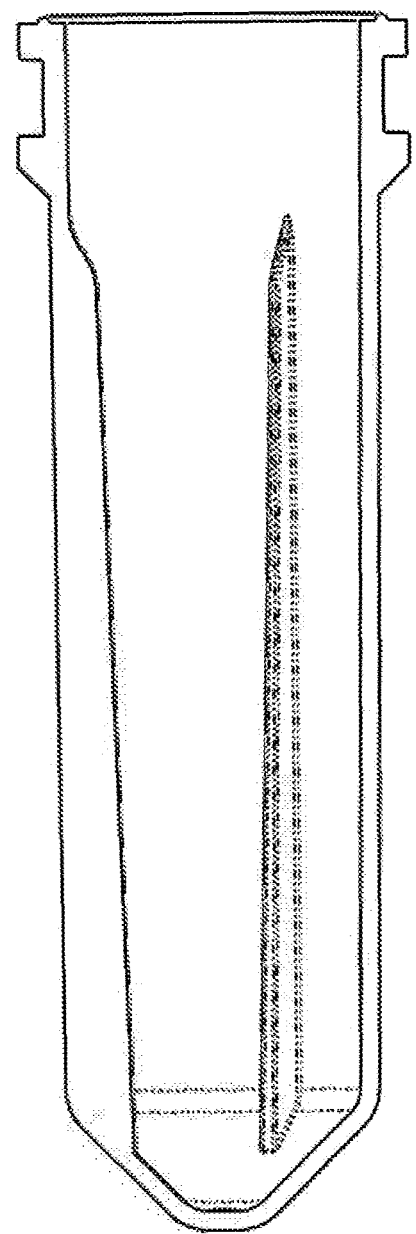
FIG. 5A is a cut-away side perspective view of one example of a container according to the present invention.
Figure 5B:
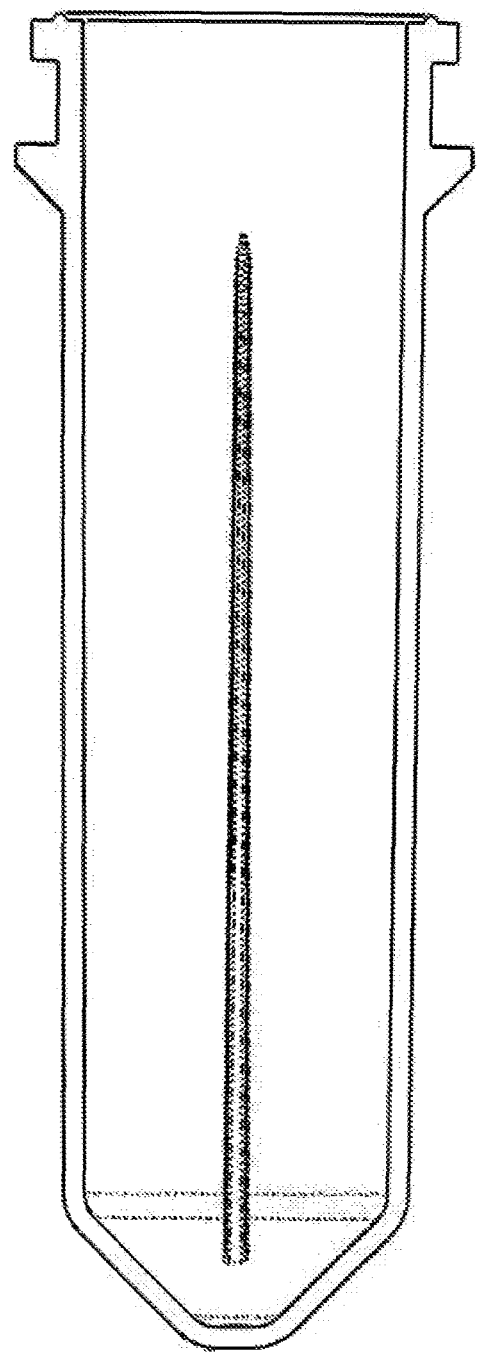
FIG. 5B is a cut-away side perspective view of the container in FIG. 5A, rotated about a vertical axis.

The containers of the present invention with substantially circular cross sections may have an interior chamber including 2 to 6 substantially linear protrusions (e.g., 2, 3, 4, 5, or 6 substantially linear protrusions). In some embodiments, the interior chamber includes 2 to 4 substantially linear protrusions. The protrusions may, in some cases, be evenly spaced within the interior chamber of the container. An example of a container of the invention with a substantially circular cross section and three evenly spaced substantially linear protrusions is depicted in FIGS. 1A and 1B.

Figures 10A, 10B:
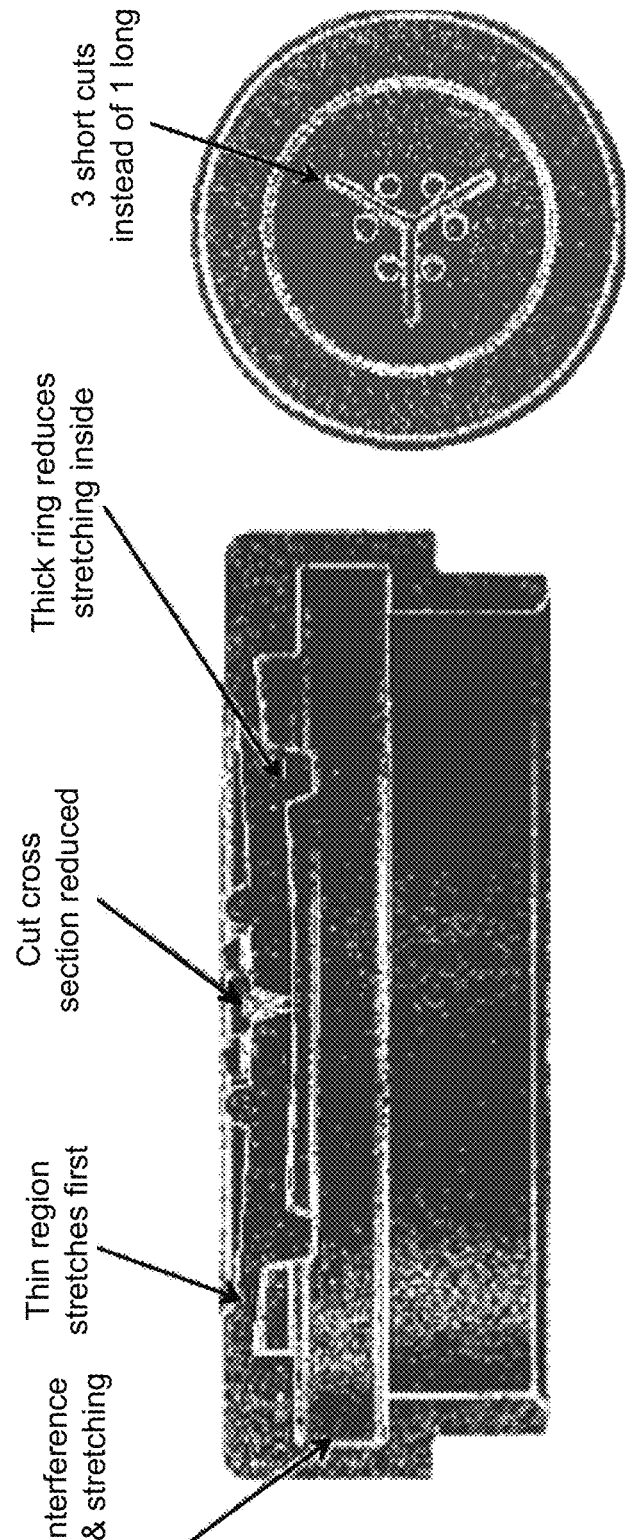
FIG. 10A is a cut-away side perspective view of a cover for a container of the invention, depicting the relative size and position of a weighted ring in the interior surface of the cover.
FIG. 10B is a schematic top perspective view of a cover for a container of the invention, showing the relative position of a tri-slit passage and six protuberances.

The containers of the present invention may additionally include a cover (e.g., a cap, lid, or top). The cover may be completely closed or include a passage that extends from its exterior surface to its interior surface. In addition to the passage, the cover may also not form an air-tight seal along the edges of a properly positioned container. The passage may include, for example, three evenly spaced slits (e.g., a tri-slit) that converge at a central axis of the cover. The tri-slit may, for example, include short radial cuts, which stop short of reaching the edge of the cover. Compared to a single side-to-side slit, the tri-slit may, for example, stretch less and open less by a force acting to open the passage (e.g., insertion of a pipette tip). In some embodiments, the cover additionally includes one or more protuberances (e.g., 2, 3, 4, 5, or 6 protuberances), or bumps, between the around or about the slit or slits (e.g., three evenly spaced slits). In other embodiments, the interior surface may include a weighted ring that encircles the slit or slits. The one or more protuberances of the exterior surface and the weighted ring of the interior surface promote closure of the passage (e.g., closure upon breaching of the passage to gain access to the interior chamber by, e.g., a pipette tip or a needle). FIGS. 10A and 10B depict one example of a cover for a container of the invention. In this example, the cover is circular and includes a tri-slit passage, two protuberances between each slit (six total), and a weighted ring to reduce stretching of the interior surface of the cover.

The containers of the present invention may additionally include a penetrable seal residing underneath the cover. The penetrable seal may easily be punctured with a pipette tip or other device to either deliver or remove fluid from the container. This seal may consist of foil, paper, plastic, or other material that has a plastic coating (e.g., a preferred embodiment is foil with a polypropylene layer) on one side. The foil is placed on the top of the rounded edge of the unsealed container, and heat is applied to flatten the container top and to form an airtight seal between the foil and the container. The seal is in place underneath the cover to reduce or ablate evaporation of fluids in the container prior to use.

Containers with Polygonal Cross Sections

As depicted in FIGS. 7A-9B and 9E-9J, the containers of the present invention may alternatively include an interior chamber with a central axis, a top with an opening, and a substantially polygonal cross section, wherein the radius of the cross section is the distance from the central axis to a corner point. The containers may, for example, have substantially angular corners within the interior chamber that support efficient mixing of a liquid sample and/or cell lysis in a liquid sample. For example, in a bead beating lysis procedure, the angular corners may prevent the rigid particles (e.g., beads) from unproductively circulating around the diameter of the tube under the force of the agitation unit (e.g., the vortexer).

The containers of the invention with polygonal cross sections may optionally include the substantially linear protrusions on the polygon sides, as described above for the containers with substantially circular cross sections. The substantially polygonal cross sections may, for example, be substantially triangular, quadrilateral, pentagonal, hexagonal, heptagonal, octagonal, nonagonal, decagonal, or dodecagonal. In some instances, the sides of the polygonal cross section may be curved (see, e.g., FIGS. 9F and 9G). Although the interior chamber includes a region with a substantially polygonal cross section, all or a portion of the exterior of the tube may be substantially circular (e.g., for use with traditional cylindrical and/or conical tube holders in, e.g., a centrifuge unit). As depicted in FIGS. 7A-8D, the containers with polygonal cross sections may, for example, retain a top half with a circular opening. This feature enables all containers of the invention to potentially have uniform circular openings, thus enabling the containers to be easily handled by an automated robotic arm (e.g., a gripper). As described above for the containers with circular cross sections, the containers of the invention with polygonal cross sections may additionally include a cover, which securely seals the top opening of the container. In embodiments in which the top of the container is polygonal, the cover will typically have the same general cross-sectional shape.

Methods for Mixing or Lysing

The present invention also includes methods for mixing a liquid sample or lysing cells (e.g., fungal cells) in a liquid sample using the containers of the invention. In one aspect, a liquid sample may be mixed by agitating the liquid in a container of the invention (e.g., a container with a substantially circular or polygonal cross section, as described above) using an agitation device (e.g., a vortexer), thereby mixing the liquid sample. In another aspect, a liquid sample may be mixed by (i) providing liquid in a container of the invention (e.g., a container with a substantially circular or polygonal cross section, as described above), where the liquid comprises rigid particles (e.g., beads), and (ii) agitating the liquid in the container with an agitation device (e.g., a vortexer), thereby mixing the liquid sample. The substantially linear protrusions and/or substantially angular corners within the interior chambers of the containers of the invention support efficient mixing of a liquid sample.

In other aspects, cells in a liquid sample may be lysed by providing the liquid sample in a container of the invention (e.g., a container with a substantially circular or polygonal cross section, as described above), where the liquid includes rigid particles (e.g., beads) and cells (e.g., fungal cells), and agitating the liquid in the container with an agitation device (e.g., a vortexer), wherein the agitation is of a sufficient force and duration to lyse the cells.

In any of the methods for mixing or lysing cells, the rigid particles (e.g., beads) may have a diameter of between about 0.2 mm to 1 mm (e.g, between about 0.1 to 0.3 mm, between about 0.3 to 0.5 mm, between about 0.5 to 0.7 mm, between about 0.7 to 0.9 mm, or between about 0.9 to 1 mm). In some embodiments, the rigid particles have a diameter of 0.8 mm. The rigid particles may, for example, be 0.5-mm glass beads, 0.1-mm silica beads, 0.7-mm silica beads, or a mixture of differently sized beads (e.g., beads, shards, glass rods, and glass disks). The agitation device (e.g., vortexer) used to facilitate mixing or lysing cells may, for example, agitate in a linear, planetary, vertical orbit, or pulsed motion.

Methods for Detecting the Presence of a Target Nucleic Acid in a Whole Blood Sample The detection of a biological analyte (e.g., a nucleic acid) in a sample may require that the analyte is first extracted from a biological organism in the sample. For biological organisms with particularly filamentous cell walls (e.g., yeast, bacteria, and algae), a robust method of cellular disruption (e.g., bead beating) must be employed to extract an intracellular target analyte. In some instances, the biological analyte may be present at a low concentration in the sample due to the sample having a low concentration of the biological organism. For example, if a subject was recently infected with a biological organism, such as the fungus *Candida albicans*, the concentration of the microorganism in a blood sample from the subject may be low. Accordingly, the ability to efficiently lyse the biological organism and detect the target analyte with high sensitivity is critically important.

The present invention features a method for detecting the presence of a target nucleic acid (e.g., a target nucleic acid from a fungus, e.g., a *Candida* genus fungus) in a whole blood sample, the method including: (i) providing an extract produced by lysing the red blood cells in a whole blood sample from a subject (e.g., a human), centrifuging the sample to form a supernatant and a pellet, discarding some or all of the supernatant, and resuspending the pellet (e.g., the pellet containing the fungal cells); (ii) lysing cells in the extract, the lysing including combining the extract with rigid particles (e.g., beads or shards as described above) to form a mixture in a container of the invention (e.g., a container with a substantially circular or polygonal cross section, as described above), and agitating the mixture with an agitation device (e.g., a vortexer) to form a lysate; (iii) providing the lysate of step (ii) in a detection tube and amplifying the nucleic acids therein to form an amplified lysate solution including from 40% (w/w) to 95% (w/w) the target nucleic acid (e.g., from 40% to 60%, 60% to 80%, 80% to 90%, or 90% to 95% (w/w) target nucleic acid) and from 5% (w/w) to 60% (w/w) nontarget nucleic acid (e.g., from 5% to 20%, 20% to 35%, 35% to 40%, or 40% to 60% (w/w) target nucleic acid); and (iv) detecting the amplified target nucleic acid.

The invention also features a method for detecting the presence of a target nucleic acid (e.g., a target nucleic acid from a fungus, e.g., a *Candida* genus fungus) in a whole blood sample, the method including: (i) providing an extract produced by lysing the red blood cells in a whole blood sample from a subject (e.g., a human), centrifuging the sample to form a supernatant and a pellet, discarding some or all of the supernatant, and resuspending the pellet (e.g., the pellet containing the fungal cells) to form an extract; (ii) lysing cells in the extract, the lysing including combining the extract with rigid particles (e.g., the beads, as described above) to form a mixture in a container of the invention (e.g., a container with a substantially circular or polygonal cross section, as described above), and agitating the mixture with an agitation device (e.g., a vortexer) to form a lysate; (iii) placing the lysate of step (ii) in a detection tube and amplifying nucleic acids therein to form an amplified lysate solution comprising from 40% (w/w) to 95% (w/w) the target nucleic acid (e.g., from 40% to 60%, 60% to 80%, 80% to 90%, or 90% to 95% (w/w) target nucleic acid) and from 5% (w/w) to 60% (w/w) nontarget nucleic acid (e.g., from 5% to 20%, 20% to 35%, 35% to 40%, or 40% to 60% (w/w) target nucleic acid); (iv) following step (iii), providing from $1 \times 10^6$ to $1 \times 10^{13}$ magnetic particles per milliliter (e.g., from $1 \times 10^6$ to $1 \times 10^8$, $1 \times 10^7$ to $1 \times 10^8$, $1 \times 10^7$ to $1 \times 10^9$, $1 \times 10^8$ to $1 \times 10^{10}$, $1 \times 10^9$ to $1 \times 10^{11}$, or $1 \times 10^{10}$ to $1 \times 10^{13}$ magnetic particles per milliliter) of the amplified lysate solution, wherein the magnetic particles have a mean diameter of from 700 nm to 1200 nm (e.g., from 700 to 850, 800 to 950, 900 to 1050, or from 1000 to 1200 nm) and binding moieties on their surface, the binding moieties operative to alter aggregation of the magnetic particles in the presence of the target nucleic acid or a multivalent binding agent; (v) placing the detection tube in a device, the device including a support defining a well for holding the detection tube including the magnetic particles and the target nucleic acid, and having an RF coil disposed about the well, the RF coil configured to detect a signal produced by exposing the liquid sample to a bias magnetic field created using one or more magnets and an RF pulse sequence; (vi) exposing the sample to a bias magnetic field and an RF pulse sequence; (vii) following step (vi), measuring the signal from the detection tube; and (viii) on the basis of the result of step (vii), detecting the target nucleic acid, wherein step (vii) is carried out without any prior purification of the amplified lysate solution. Additional methods and reagents (e.g., probes specific for *Candida*) are described in U.S. patent application Ser. No. 13/363,916, which hereby incorporated by reference.

Detection of a Fungal Infection in a Subject

The compositions of the invention enable methods of monitoring and diagnosing infectious disease in a multiplexed, automated, no sample preparation system. Such systems and methods could be used to monitor, for example, fungal infection, such as candidemia. Early diagnosis of candidemia is clinically important as this type of infection, if left untreated, can lead to a variety of different symptoms (depending on the area of the body affected) including, but not limited to, lesions and sores of the mouth, bleeding gums, burning with urination, vaginal irritation, vaginal itching, diarrhea, nausea, and vomiting. *Candida* infections are increasingly important pathogens in the NICU. Risk factors for the development of candidemia in neonates include gestational age less than 32 weeks, 5-min Apgar scores of less than 5, shock, disseminated intravascular coagulopathy, prior use of intralipids, parenteral nutrition administration, CVL use, H2 blocker administration, intubation, or length of stay longer than 7 days.

In general, a whole blood sample may be taken from a suspected candidemia subject, and the presence of, for example, a targeted conserved *Candida* genomic region may be detected by use of the methods of the invention described in detail above.

EXAMPLE

The following example is provided for the purpose of illustrating the invention and is not meant to limit the invention in any way.

Example 1. Increased Cell Lysis Using Containers with Substantially Linear Protrusions The efficiency of fungal cell lysis using 2.8-ml containers of the invention including three evenly spaced substantially linear protrusions ("fins") was compared to the efficiency achieved with standard 2.8-ml containers. Eight isolates of fungal cells (at a concentration of 3 cells/mL) were tested in duplicate in the two types of containers. To each of the containers, 0.7-mm Zirconia beads were added and the containers were agitated with a vortexer at 2800 rpm (+/−400 rpm) for 8 minutes for the containers of the invention including the three protrusions or 2000 rpm (+/−400 rpm) for 5 minutes for the standard 2.8-ml containers. Following the bead beating procedure, an aliquot of each lysate was then subjected to PCR amplification by addition of the lysate to a PCR master mix including nucleotides; buffer (5 mM $(NH_4)SO_4$, 3.5 mM $MgCl_2$, 6% glycerol, 60 mM Tricine, pH=8.7); primers specific for *Candida* (forward primer in 4× excess to allow for asymmetric single-strand production in the final product); and thermostable polymerase (HemoKlenTaq (New England Biolabs)). Magnetic particles conjugated to nucleic acids, each with sequence complementary to a portion of the amplified target such that the magnetic particles aggregate in the presence of the target nucleic acid, were added to the PCR amplification reaction. The amplified target *Candida* nucleic acid was then detected by measuring T2 relaxation times (msec). If all other variables in the detection assay have approximately equal contributions, then the difference in detection of the target nucleic acid may be directly correlated with the efficiency of cell lysis.

Figure 11:
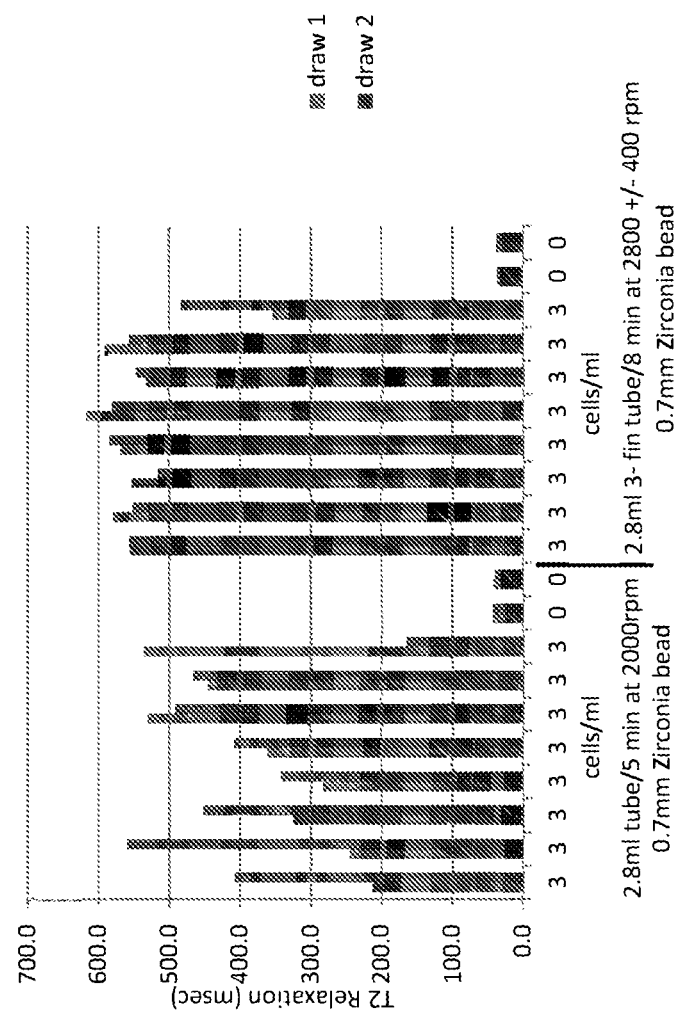
FIG. 11 is a graph showing the amount of *Candida* cell lysis in a standard bead beating assay is consistently higher using containers of the invention including three substantially linear protrusions, or "fins," compared to standard containers without linear protrusions.

As depicted in FIG. 11, the data indicate that increased detection of the target nucleic acid is observed for *Candida* cells lysed in containers of the invention having three protrusions compared to that obtained from standard containers without protrusions. The data show that T2 relaxation times measuring target nucleic acid levels from the former group were uniformly higher than the T2 measurements obtained from the latter group. Both groups showed T2 signals significantly higher than that obtained from the four control experiments in each group. In sum, the data indicate that the containers of the invention increase the efficiency of cell lysis (e.g., in a bead beating assay) relative to standard containers known in the art.

Other Embodiments

All publications, patents, and patent applications mentioned in the above specification are hereby incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A method of lysing cells in a liquid sample, said method comprising:
    (a) providing liquid in a container comprising: (i) an interior chamber with a central axis, (ii) a top comprising an opening, and (iii) a substantially circular cross section or a substantially polygonal cross section, wherein the surface of said interior chamber comprises one or more substantially linear protrusions substantially parallel to said central axis, and wherein said liquid comprises rigid particles and cells; and
    (b) agitating said liquid in said container,
    wherein said agitation is of a sufficient force and duration to lyse said cells.

2. The method of claim 1, wherein the substantially linear protrusions have a length substantially parallel to said central axis, a depth substantially parallel to the radius of said substantially circular or polygonal cross section, and a width substantially perpendicular to said radius, wherein said depth increases from top to bottom of the substantially linear protrusions and said width increases from top to bottom of the substantially linear protrusions, and wherein the depth of the substantially linear protrusions is greater than 10% of the radius at some point along the length of the substantially linear protrusions.

3. The method of claim 2, wherein said container comprises a substantially polygonal cross section having a radius, wherein said radius is the distance from said central axis to a corner point, and wherein the surface of said interior chamber additionally comprises one or more substantially linear protrusions substantially parallel to said central axis.

4. The method of claim 2, wherein said container comprises a substantially polygonal cross section having a radius, wherein said radius is the distance from said central axis to a corner point, and wherein said substantially polygonal cross section is substantially triangular, quadrilateral, pentagonal, hexagonal, heptagonal, octagonal, nonagonal, decagonal, or dodecagonal.

5. The method of claim 1, wherein said interior chamber comprises 2 to 6 substantially linear protrusions.

6. The method of claim 1, wherein said rigid particles have a diameter of between 0.1 mm to 1 mm.

7. A method of detecting the presence of a target nucleic acid in a whole blood sample, the method comprising:
    (a) providing an extract produced by: (a1) lysing the red blood cells in a whole blood sample from a subject, (a2) centrifuging the sample to form a supernatant and a pellet, (a3) discarding some or all of the supernatant, and (a4) resuspending the pellet to form an extract, wherein the extract comprises one or more additional cells;
    (b) lysing said additional cells in said extract, said lysing of said additional cells comprising (b1) combining the extract with rigid particles to form a mixture in a container comprising: (i) an interior chamber with a central axis, (ii) a top comprising an opening, and (iii) a substantially circular cross section or a substantially polygonal cross section, wherein the surface of said interior chamber comprises one or more substantially linear protrusions substantially parallel to said central axis; and (b2) agitating the mixture at a sufficient force and duration to lyse said additional cells, thereby forming a lysate;
    (c) providing the lysate of step (b) in a detection tube and amplifying nucleic acids therein to form an amplified lysate solution comprising from 40% (w/w) to 95% (w/w) the target nucleic acid and from 5% (w/w) to 60% (w/w) nontarget nucleic acid; and
    (d) detecting the amplified target nucleic acid.

8. The method of claim 7, wherein the substantially linear protrusions have a length substantially parallel to said central axis, a depth substantially parallel to the radius of said substantially circular or polygonal cross section, and a width substantially perpendicular to said radius, wherein said depth increases from top to bottom of the substantially linear protrusions and said width increases from top to bottom of the substantially linear protrusions, and wherein the depth of the substantially linear protrusions is greater than 10% of the radius at some point along the length of the substantially linear protrusions.

9. The method of claim 8, wherein said container comprises a substantially polygonal cross section having a radius, wherein said radius is the distance from said central axis to a corner point, and wherein the surface of said interior chamber additionally comprises one or more substantially linear protrusions substantially parallel to said central axis.

10. The method of claim 9, wherein said container comprises a substantially polygonal cross section having a radius, wherein said radius is the distance from said central axis to a corner point, and wherein said substantially polygonal cross section is substantially triangular, quadrilateral, pentagonal, hexagonal, heptagonal, octagonal, nonagonal, decagonal, or dodecagonal.

11. The method of claim 7, wherein said interior chamber comprises 2 to 6 substantially linear protrusions.

12. The method of claim 7, wherein said rigid particles have a diameter of between 0.1 mm to 1 mm.

13. A method of amplifying a target nucleic acid in a whole blood sample, the method comprising:
(a) providing an extract produced by: (a1) lysing the red blood cells in a whole blood sample from a subject, (a2) centrifuging the sample to form a supernatant and a pellet, (a3) discarding some or all of the supernatant, and (a4) resuspending the pellet to form an extract, wherein the extract comprises one or more additional cells;
(b) lysing said additional cells in said extract, said lysing of said additional cells comprising: (b1) combining the extract with rigid particles to form a mixture in a container comprising: (i) an interior chamber with a central axis, (ii) a top comprising an opening, and (iii) a substantially circular cross section or a substantially polygonal cross section, wherein the surface of said interior chamber comprises one or more substantially linear protrusions substantially parallel to said central axis; and (b2) agitating the mixture at a sufficient force and duration to lyse said additional cells, thereby forming a lysate; and
(c) providing the lysate of step (b) in a detection tube and amplifying nucleic acids therein to form an amplified lysate solution comprising from 40% (w/w) to 95% (w/w) the target nucleic acid and from 5% (w/w) to 60% (w/w) nontarget nucleic acid.

14. The method of claim 13, wherein the substantially linear protrusions have a length substantially parallel to said central axis, a depth substantially parallel to the radius of said substantially circular or polygonal cross section, and a width substantially perpendicular to said radius, wherein said depth increases from top to bottom of the substantially linear protrusions and said width increases from top to bottom of the substantially linear protrusions, and wherein the depth of the substantially linear protrusions is greater than 10% of the radius at some point along the length of the substantially linear protrusions.

15. The method of claim 14, wherein said container comprises a substantially polygonal cross section having a radius, wherein said radius is the distance from said central axis to a corner point, and wherein the surface of said interior chamber additionally comprises one or more substantially linear protrusions substantially parallel to said central axis.

16. The method of claim 14, wherein said container comprises a substantially polygonal cross section having a radius, wherein said radius is the distance from said central axis to a corner point, and wherein said substantially polygonal cross section is substantially triangular, quadrilateral, pentagonal, hexagonal, heptagonal, octagonal, nonagonal, decagonal, or dodecagonal.

17. The method of claim 13, wherein said interior chamber comprises 2 to 6 substantially linear protrusions.

18. The method of claim 13, wherein said rigid particles have a diameter of between 0.1 mm to 1 mm.

* * * * *